(12) United States Patent
Luan et al.

(10) Patent No.: US 9,372,171 B2
(45) Date of Patent: *Jun. 21, 2016

(54) NANOPORE SENSOR FOR DETECTING MOLECULAR INTERACTIONS

(71) Applicant: INTERNATIONAL BUSINESS MACHINES CORPORATION, Armonk, NY (US)

(72) Inventors: Binquan Luan, Chappaqua, NY (US); Ruhong Zhou, Stormville, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 476 days.

This patent is subject to a terminal disclaimer.

(21) Appl. No.: 13/873,815

(22) Filed: Apr. 30, 2013

(65) Prior Publication Data

US 2014/0318968 A1    Oct. 30, 2014

(51) Int. Cl.
G01N 27/447        (2006.01)
G01N 33/487        (2006.01)
B82Y 30/00         (2011.01)

(52) U.S. Cl.
CPC .... G01N 27/44791 (2013.01); G01N 33/48721 (2013.01); B82Y 30/00 (2013.01)

(58) Field of Classification Search
CPC ..... H04M 3/4221; A01M 1/00; A01M 23/00; A01M 23/02; A01M 23/16; A01M 23/38; G01N 33/48721; G01N 27/447; G01N 27/44756; C07K 1/26
USPC ............ 43/61, 121, 74, 58; 375/322; 221/197
See application file for complete search history.

(56) References Cited

U.S. PATENT DOCUMENTS

| 7,005,264 | B2 | 2/2006 | Su et al. |
| 7,468,271 | B2 | 12/2008 | Golovchenko et al. |
| 7,846,738 | B2 | 12/2010 | Golovchenko et al. |
| 7,993,524 | B2 | 8/2011 | Ratto et al. |
| 8,246,995 | B2 | 8/2012 | Dai et al. |
| 2008/0008760 | A1 | 1/2008 | Bianco et al. |
| 2008/0193490 | A1 | 8/2008 | Hirsch et al. |

(Continued)

FOREIGN PATENT DOCUMENTS

WO    WO2010042514 A1    4/2010

OTHER PUBLICATIONS

Zhao et al., "Detecting SNPs Using a Synthetic Nanopore", NanoLetters 2007 vol. 7, No. 6, 1680-1685.*

(Continued)

*Primary Examiner* — Alexander Noguerola
(74) *Attorney, Agent, or Firm* — Tutunjian & Bitetto, P.C.; Vazken Alexnanian

(57) ABSTRACT

A nanosensor for detecting molecule characteristics includes a membrane having an opening configured to permit a charged carbon nanotube to pass but to block a molecule attached to the carbon nanotube. The opening is filled with an electrolytic solution. An electric field generator is configured to generate an electric field relative to the opening to drive the charged carbon nanotubes through the opening. A sensor circuit is coupled to the electric field generator to sense current changes due to charged carbon nanotubes passing into the opening, and to bias the electric field generator to determine a critical voltage related to a force of separation between the carbon nanotube and the molecule.

6 Claims, 7 Drawing Sheets

(56) References Cited

U.S. PATENT DOCUMENTS

2012/0219985 A1     8/2012    Yoon et al.
2012/0261261 A1    10/2012    Huber

OTHER PUBLICATIONS

Comer et al., "Toward detection of DNA-bound proteins using solid-state nanopores:Insights from computer simulations", Electrophoresis 2012, 33, 3466-3479.*

Hall et al., "Translocation of Single-Wall Carbon Nanotubes Through Solid-State Nanopores", NanoLetters 2011, 11, 2446-2450.*

Ge, C., et al. "Binding of Blood Proteins to Carbon Nanotubes Reduces Cytotoxicity" PNAS, vol. 108, No. 41. Oct. 2011. pp. 16968-16973.

King, G., et al. "Probing Nanotube-Nanopore Interactions" Physical Review Letters, vol. 95. Nov. 2005. (4 Pages).

Luan, B., et al. "Nanopore-Based Sensors for Detecting Toxicity of a Carbon Nanotube to Proteins" J Phys. Chem. Lett., vol. 3, No. 17. Aug. 2012. pp. 1-15.

Nel, A., et al. "Toxic Potential of Materials at the Nanolevel" Science, vol. 311, No. 5761. Feb. 2006. pp. 622-627.

Porter, A., et al. "Direct Imaging of Single-Walled Carbon Nanotubes in Cells" Nature Nanotechnology, vol. 2. Oct. 2007. pp. 713-717.

Yeh, I., et al. "Nucleic Acid Transport Through Carbon Nanotube Membranes" PNAS, vol. 101, No. 33. Aug. 2004. pp. 12177-12182.

Zuo, G., et al. "Plugging Into Proteins: Poisoning Protein Function by a Hydrophobic Nanoparticle" ACS Nano, vol. 4, No. 12. Nov. 2010. pp. 7508-7514.

Luan, B., et al. "Nanopore Device for Drug-Like Molecule Screening or Lead Optimization to a Targeted Protein" U.S. Appl. No. 13/873,854, filed Apr. 30, 2013. (24 Pages).

* cited by examiner

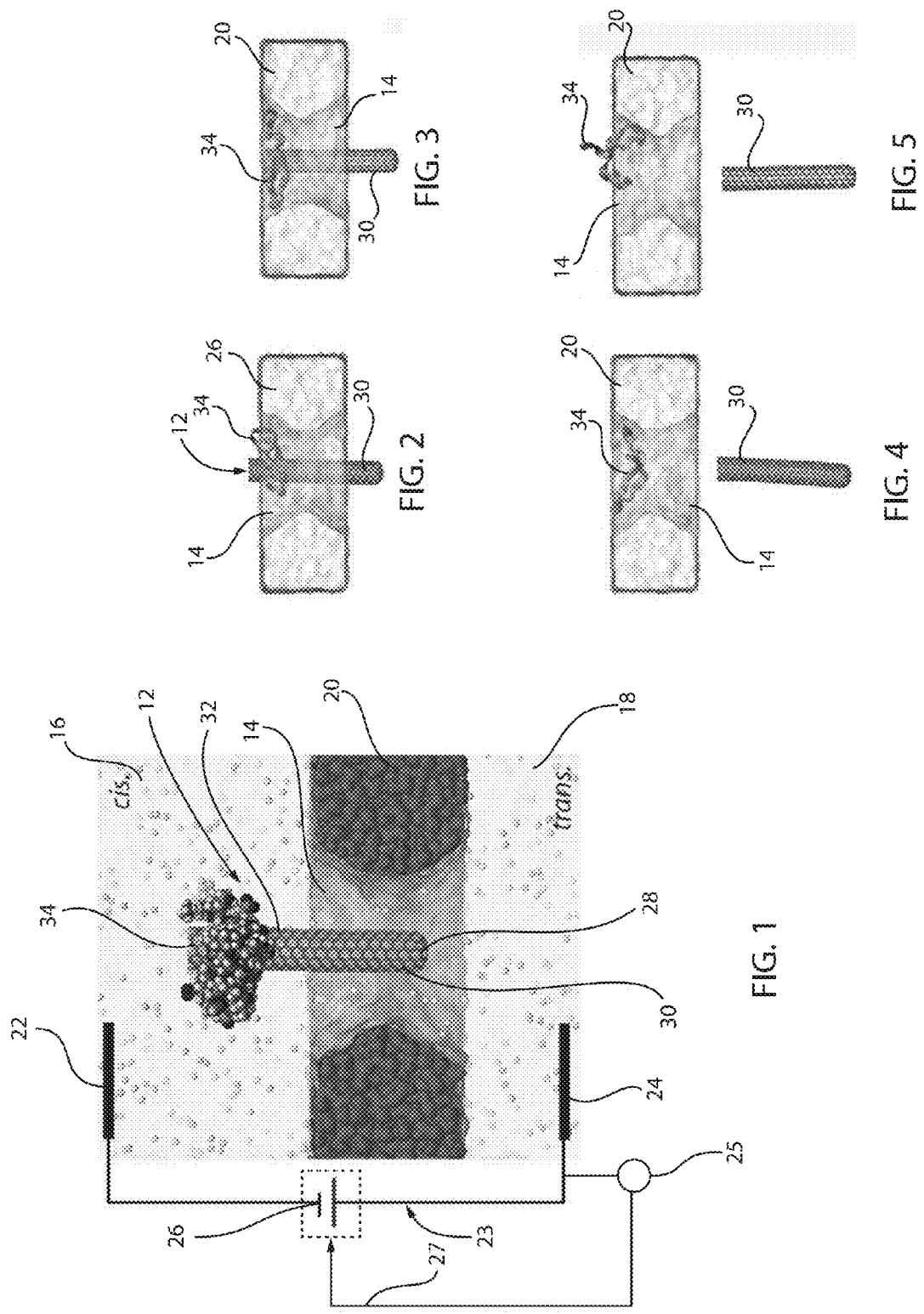

NANOPORE SENSOR FOR DETECTING MOLECULAR INTERACTIONS

RELATED APPLICATION INFORMATION

This application is related to commonly assigned U.S. patent application Ser. No. 13/873,854 filed on Apr. 30, 2013, incorporated herein by reference in its entirety.

BACKGROUND

1. Technical Field

The present invention relates to sensors, and more particularly to a nanopore sensor and methods for detecting interaction between carbon nanotubes and proteins.

2. Description of the Related Art

Accompanied with fast-paced developments and applications of carbon-based nanomaterials, such as carbon nanotubes (CNTs), growing concerns of bio-safety of these nanomaterials to a human body have led to strategic research into nanotoxicity. It has been found experimentally that a CNT can pass a cell membrane and subsequently enter the cytoplasm and nucleus, causing cell mortality. A carbon nanotube (CNT) can be toxic to a living cell by binding to proteins and then impairing their functionalities; however, an efficient screening method that examines binding capability of a CNT to protein molecules in vitro is still unavailable. At a molecular level, the nanotoxicity can result from strong interactions between a CNT and a protein molecule, such as an insertion of a CNT into the ligand-binding site of a protein molecule. Consequently, a malfunction of the affected protein molecule occurs in cell metabolism.

On the other hand, the interaction between CNT and proteins could be beneficial. For example, CNT-based drug molecules can be used to competitively interact with proteins of a virus, preventing the virus from attacking cells of human, animals or plants.

SUMMARY

A nanosensor for detecting molecule characteristics includes a membrane having an opening configured to permit a charged carbon nanotube to pass but to block a molecule attached to the carbon nanotube. The opening is filled with an electrolytic solution. An electric field generator is configured to generate an electric field relative to the opening to drive the charged carbon nanotubes through the opening. A sensor circuit is coupled to the electric field generator to sense current changes due to charged carbon nanotubes passing into the opening, and to bias the electric field generator to determine a critical voltage related to a force of separation between the carbon nanotube and the molecule.

A nanosensor for detecting protein toxicity includes a membrane having one or more openings, each opening being configured to permit a charged carbon nanotube to pass but to block a protein molecule attached to the carbon nanotube. The opening is filled with an electrolytic solution. An electric field generator is configured to generate an electric field relative to the opening to drive the charged carbon nanotubes through the opening. A sensor circuit is coupled to the electric field generator to sense current changes due to charged carbon nanotubes passing into the opening, and to bias the electric field generator to determine a critical voltage value for rupture between the carbon nanotube and the molecule. The critical voltage value is determined to infer interaction strength between the carbon nanotube and the molecule.

A method for detecting molecule characteristics includes generating an electric field across a membrane having an opening to drive charged carbon nanotubes through the opening, the opening being configured to permit the charged carbon nanotube to pass but to block a molecule attached to the carbon nanotube, the opening being filled with an electrolytic solution; sensing current changes due to charged carbon nanotubes passing into or through the opening; biasing the electric field to measure a voltage at a point of separation between the carbon nanotube and the molecule; and correlating the voltage to measure a characteristic of the molecule.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 1 is a cross-sectional view of a nanopore-based toxicity sensor in accordance with one embodiment;

FIG. 2 shows a cross-sectional view of a nanopore-based toxicity sensor prior to separation between the carbon nanotube and a protein in accordance with one embodiment;

FIG. 3 shows a cross-sectional view of the nanopore-based toxicity sensor after the protein is secured in the nanopore in accordance with one embodiment;

FIG. 4 shows a cross-sectional view of the nanopore-based toxicity sensor after separation between the carbon nanotube and the protein in accordance with one embodiment;

FIG. 5 shows a cross-sectional view of the nanopore-based toxicity sensor after further separation between the carbon nanotube and the protein in accordance with one embodiment;

DETAILED DESCRIPTION OF PREFERRED EMBODIMENTS

Figure 6:
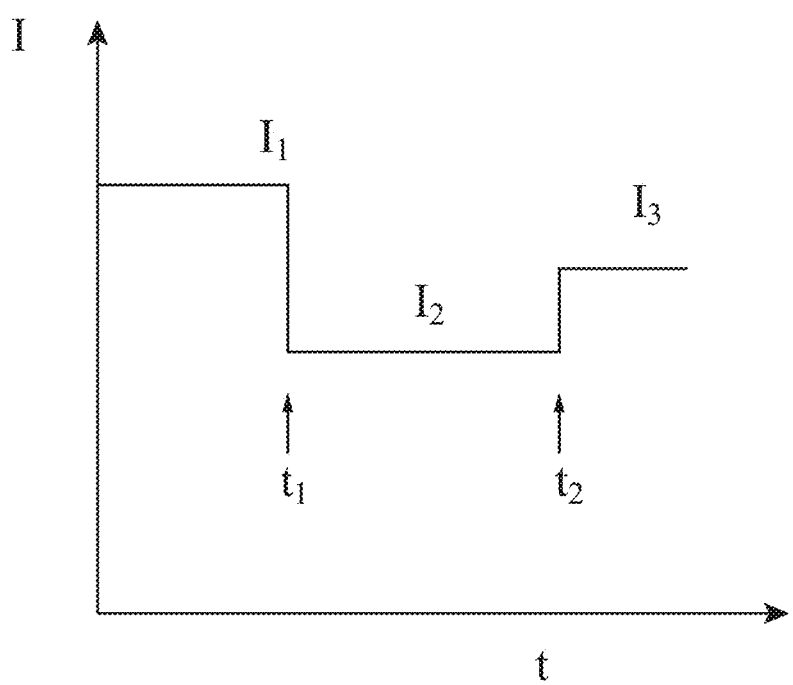
FIG. 6 is a graph showing time-dependent ionic-current signals when electrically driving a CNT-protein complex through a nanopore in accordance with one embodiment.

Studying interactions of carbon based nanotubes (CNT) to protein complexes remains challenging. In accordance with the present principles, an ultra-sensitive (e.g., for a binding energy of a few $k_B T$ (e.g., 1-10) between CNT and protein) and high-throughput (or high-speed) sensor is provided that can accelerate studies in this field. Methods and devices are provided for detecting toxicity of a CNT to protein using a nanopore (a nanometer-sized hole in a thin membrane). In another embodiment, toxicity can be detected using multiple nanopores, using a fluid channel or multiple fluid channels.

Methods and devices for screening the toxicity of a CNT to proteins are also provided by measuring the strength of a bond between the CNT and the protein, since at the molecular level, the nanotoxicity can result from strong interactions between the CNT and the protein molecule. Similar methods may be employed for other molecule, such as, e.g., single biological molecules, such as DNA, microRNA and etc.

It is to be understood that the present invention will be described in terms of a given illustrative architecture; however, other architectures, structures, materials and process features and steps may be varied within the scope of the present invention.

It will also be understood that when an element such as a layer, region, material or device is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, a cross-sectional view of a carbon nanotube (CNT)-protein complex 12 moving through a nanopore 14 is shown. The complex 12 can be prepared by mixing tested protein molecules with CNTs in an electrolyte solution. A CNT 30 or CNTs may bond into a ligand-binding site of a protein molecule 34. Two fluidic chambers 16, 18 (cis. and trans. respectively) are separated by a membrane 20 and connected via the nanopore 14. The solid membrane 20 is formed from, for example, $SiO_2$ or $Si_3N_4$ material, although other materials may be employed. The fluid chambers 16, 18 are compartments that store a solution containing test molecules. The size of the nanopore or nanochannel 14 should be larger than the size of a CNT 30 and smaller than the size of the protein molecule 34, e.g. about 3 nm in diameter. A biasing electric field circuit or field generating circuit 23 is applied across the membrane 20, by inserting two electrodes 22, 24 (such as, e.g., Ag/AgCl electrodes connected to a battery 26, other electrode types may also be employed) into cis. and trans. chambers 16, 18, respectively.

A sensor circuit 25 is coupled to the electric field generator 23 to sense current changes due to charged carbon nanotubes passing into the opening, and to bias the electric field generator 23 (control or bias the battery 26) through feedback 27 to reach and determine a critical voltage. The critical voltage, in turn, is employed to determine a force of separation between the carbon nanotube and the molecule. A biasing voltage may range from, e.g., about 100 mV to about 1 V.

The sensor 25 is coupled to the circuit 23 to measure changes in current. The sensor 25 may include known devices for accurately measuring transient currents in the circuit 23, such as a patch clamp amplifier. A first end 28 of the CNT 30 is functionalized with charged chemical groups (such as a carboxyl group or amines that are negatively charged in an electrolyte). The same end of the CNT 30 is capped so ions do not enter inside the CNT 30. A second end 32 of the CNT 30 is unmodified and can be used to test the toxicity of a protein molecule 34 although other molecules may be employed. The second end 32 is employed to bond the CNT 30 into the ligand-binding site of the protein molecule 34.

In a biasing electric field, the charged CNT 30 is electrically driven through the nanopore 14 as shown in FIGS. 2-5. FIG. 2 shows the CNT 30 attached with the protein molecule 34 as it enters the nanopore 14. The nanopore 14 is configured to have a size larger than a diameter of the CNT 30 and less than the size of the protein molecule 34. During the translocation process, as shown in FIG. 3, the protein molecule 34 is too large to move through the nanopore 14 and is stuck inside the nanopore 14. With a biasing voltage that is larger than a critical value ($V_{cr}$), the CNT 30 can be further pulled through the nanopore 14 as shown in FIGS. 4 and 5. The interaction strength (thus, the potential toxicity) between the CNT 30 and the protein molecule 34 can be inferred from the critical value $V_{cr}$ (the voltage value when the complex is ruptured). The translocation process illustrated in FIGS. 2-5 can be monitored by measuring the ionic current through the nanopore 14. Current changes will indicate when the complex 12 has entered the nanopore 14. Then a bias of the battery voltage can be performed to reach $V_{cr}$ and rupture the complex 12. The value of $V_{cr}$ can be employed to indicate strength and toxicity.

In one embodiment, a nanopore 14 drilled through the membrane has an hour-glass shape, with a pore "neck" 15 Å in radius (3-nm nanopore) and pore openings 25 Å in radius. A 1M KCl electrolyte was used on both cis. 16 and trans. 18 sides. In one example, we adopted the atomic structure of the protein-CNT complex previously studied for CNT's toxicity to a WW domain (1YJQ8, the smallest monomeric triple-stranded antiparallel beta-sheet protein domain that is stable in the absence of disulfide bonds). In the complex, a (6,6)-armchair single-wall CNT (radius ~4.1 Å) is inserted into the active site of the WW domain, which forbids the ligand binding. One open end 28 of the CNT 30 is then further "functionalized" with charged atoms to mimic the carboxyl groups. Each charged atom has 0.5 e and the total charge of the modified CNT is 10 e. The charged CNT end 28 is capped to prevent $K^+$ ions from entering the CNT. A biasing electric field, normal to the membrane surface, is applied to drive the CNT-WW complex 12 towards the nanopore 14.

During simulations, the CNT can diffuse laterally (perpendicular to the field direction), but atoms in the CNT are constrained within 5 Å from the central axis of the nanopore, permitting CNT's entry into the pore. In a biasing electric field, there exists an ionic current through the nanopore 14. The local ionic current I in the pore is calculated as $$I = \left(\sum_i q_i v_i\right) \bigg/ D,$$

where D is the membrane thickness; $q_i$ and $v_i$ are the charge and the velocity of an ion inside the pore, respectively. When the CNT-WW complex 12 was driven into the pore, the pore current decreased from an open-pore current to a blockage current. Despite the fact that the charged CNT brought its counter ions into the pore, the total number of ions inside the pore decreased. This is because ions (in a 1M electrolyte), that were physically excluded by the complex, outnumbered counter ions of the charged CNT. Therefore, the pore current is less when the complex is inside the pore. Note that the reduction of a pore current indicates an entry of the complex into the pore.

Since the WW domain is larger in size than the constriction site of the nanopore, translocation of the complex is sterically prohibited. After the entry (~12 ns) of the complex, the reduced pore-current lasts for the rest of simulation time (~150 ns). At the same biasing voltage (0.5 V), another independent simulation shows that the CNT cannot only be electrically driven into the pore but also be electrically pulled through the pore, leaving the protein molecule stuck on the pore surface. During this process, a rupture between the CNT and the WW domain occurred. The rupture process is signified by an increase of the pore current. This is expected since the blockage (by protein only) of a pore current is less after the CNT exits the pore. Therefore, 0.5 V can be considered as a critical voltage ($V_{cr}$), above which the rupture of the complex is expected. Note that the critical voltage indicates how strongly a CNT interacts with a protein molecule.

To detect the entry of the complex into the pore, the signal of current blockage ($I_{open} - I_{b1}$) needs to be larger than the noise of an open-pore current, where $I_{open}$ is the open pore current and $I_{b1}$ is the blocked pore current. We use the percentage of current blockage, i.e. ($I_{open} - I_{b1}$)/$I_{open}$, as a measure of signal quality. When $V_{bias} > V_{cr}$, the complex is farther away from the pore constriction. When $V_{bias} > V_{cr}$, the rupture of the complex occurs before the complex gets close to the pore constriction. Therefore, in both above cases, percentages of current blockage are less than that for $V_{cr}$.

Because of the hydrophobic interaction between the CNT and the protein molecule, an energy barrier needs to be overcome before the CNT can be pulled through the pore. After that, the number of contacting atoms is zero. One notable and common characteristic of these electrically driven processes is that the complex moves "slowly" when distant from the pore but moves relatively faster when close to the pore. This indicates that the biasing electric field is stronger around the pore than far away from the pore. Therefore, the electrophoretic motion of the complex is faster when the charged part of the CNT enters the pore.

To quantify the distribution of electrostatic potentials in the simulated system, Poisson equation was used to solve potentials from atomic positions and charges averaged over a 4-ns simulation. Theoretically, the ionic current is proportional to $(n^+\mu^+ + n^-\mu^-) \cdot e \cdot dV/dz \cdot S$, ignoring the contribution from gradients of ion concentrations. Here, $n^+$ and $n^-$ are concentrations of cat- and an-ions respectively; $\mu^+$ and $\mu^-$ are mobilities of cat- and an-ions respectively; e is the charge of an electron and S is a cross-section area. Since in a steady-state the ion current is constant, dV/dz is inversely proportional to the cross-section area. The cross-section area of a nanopore is usually much smaller than that of a cis. or trans. chamber, therefore the electric field (dV/dz) inside the nanopore is much larger than fields outside.

Referring to FIG. 6, time-dependent current signals during a translocation/rupture event are illustratively shown in a plot of current (I) versus time (t). At the beginning, the CNT-protein complex is outside the nanopore, $I_1$ is the open-pore current. At the time $t_1$, the complex enters the pore and the ionic current $I_2$ is reduced. This is due to the fact that the complex partially blocks the nanopore. If the biasing voltage is less than the critical value, the current remains constant at $I_2$. When the biasing voltage is larger than the critical value, the CNT is further driven through the pore, and the pore is less blocked at time $t_2$. Thus, the ionic current through the pore increases to $I_3$. Therefore, by monitoring and/or controlling a biasing voltage, it is possible to determine the critical voltage ($V_{cr}$) at which a rupture between the CNT and the protein molecule occurs. The rupture force (e.g., ~90 pN in one case) can be estimated using $q_{eff} V_{cr}/d$, where $q_{eff}$ is the effective charge of the CNT after ionic screening in an electrolyte and d is the thickness of a solid-state membrane.

Figure 7:
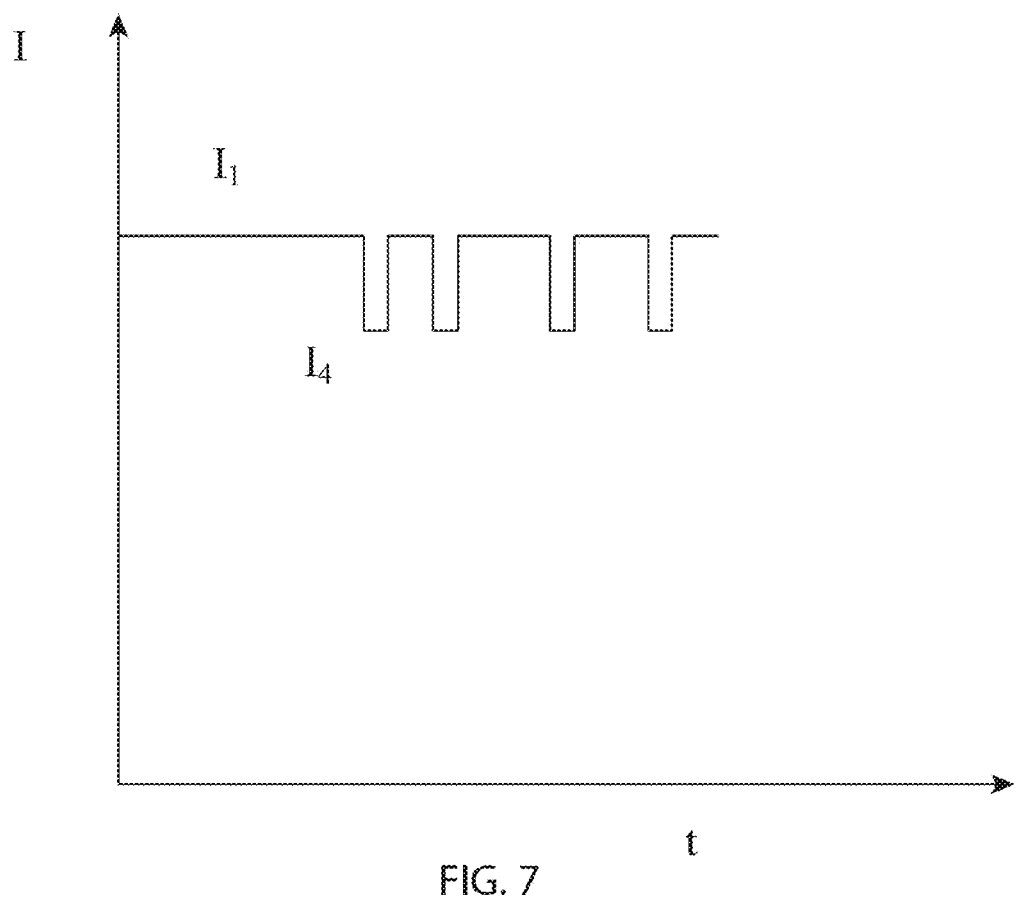
FIG. 7 is a graph showing time-dependent ionic-current signals when electrically driving CNTs through a nanopore in accordance with one embodiment.

Referring to FIG. 7, time-dependent current signals are illustratively shown in a plot of current (I) versus time (t) for CNTs driven through a nanopore without bound proteins. These events can be detected from signals of ionic currents shown in FIG. 7.

At the beginning, the CNT is outside the nanopore, $I_1$ is the open-pore current. At a later time, the CNT enters the pore and the ionic current $I_4$ is reduced. This is due to the fact that the CNT partially blocks the nanopore, but not as much as the CNT complex in FIG. 6. Since the cross-section of CNT is smaller than a complex, the current blocked by a CNT is less (e.g., in a 1M electrolyte solution). Additionally, the translocation velocity of a CNT is much faster than that of a complex. Therefore, the duration time is also less, as shown in FIG. 6. It should be noted that a 1M electrolyte solution is described but other ionic concentrations may be employed.

Figure 8:
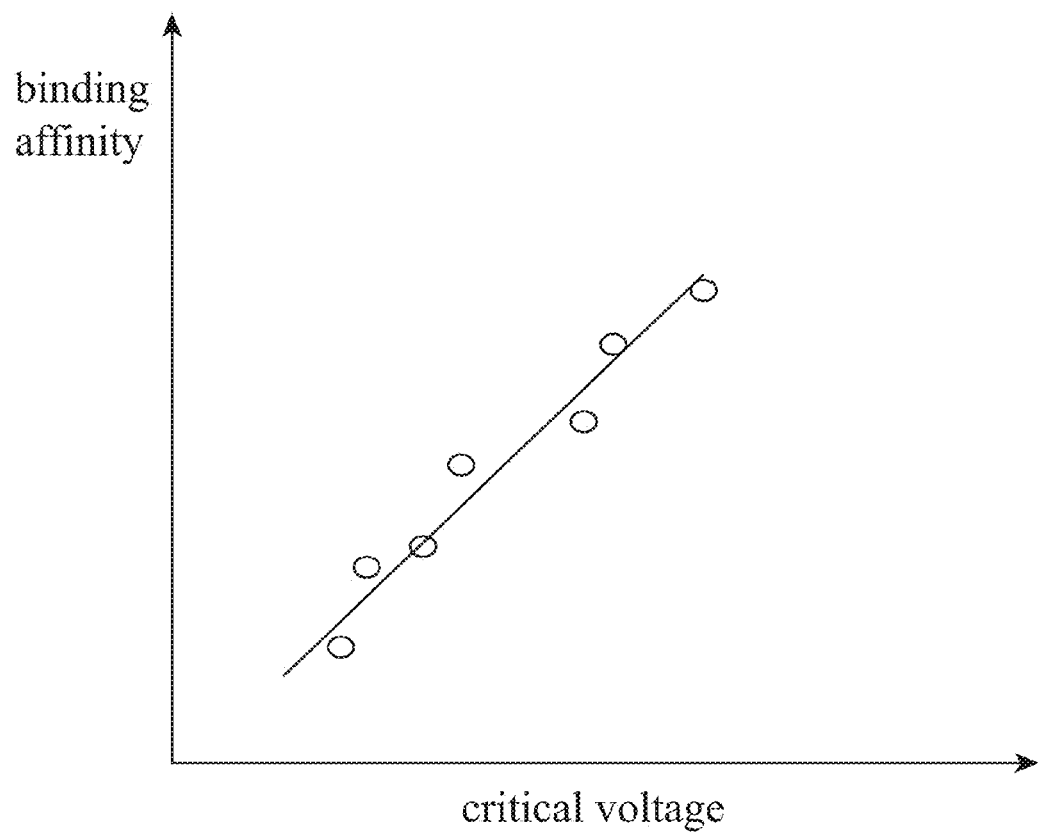
FIG. 8 is an illustrative plot showing binding affinity versus critical voltage for determining separation strength between CNTs and proteins in accordance with the present principles.

Referring to FIG. 8, a plot of binding affinity versus critical voltage illustrates a relation that can be determined experimentally or theoretically. The binding affinity can be inferred from the critical voltage ($V_{cr}$) at which the rupture between a CNT and a protein molecule occurs. This provides a high-throughput and low-cost way to determine the interaction between a CNT and a protein molecule. Binding affinity may be employed as one indication of the toxicity or other characteristic of the protein.

Figure 9:
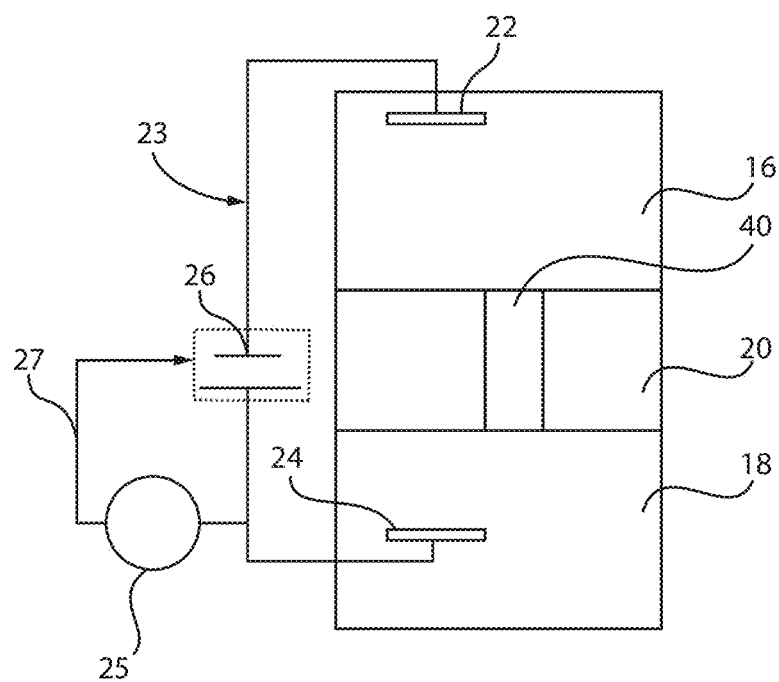
FIG. 9 is a cross-sectional view of a channel based toxicity sensor in accordance with another embodiment.

Referring to FIG. 9, another embodiment shows a planar channel 40 employed instead of a nanopore 14. The planar channel 40 is configured to permit the CNT-protein complex to be separated such that the CNT 30 passes into the channel 40, and the protein molecule 34 (not shown) does not. An electric field is applied as before with the battery 26 and electrodes 22, 24 being employed to provide the field and to measure the current changes due to the CNT-protein complex, as before. The planar channel 40 has a channel constriction size being less than that of the protein molecule 34.

Figure 10:
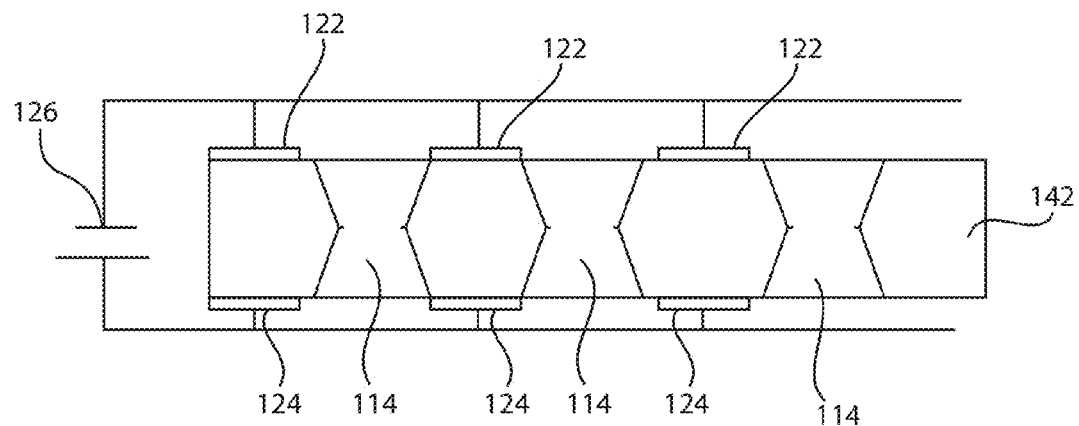
FIG. 10 is a cross-sectional view of a multiple nanopore toxicity sensor in accordance with another embodiment.
Figure 11:
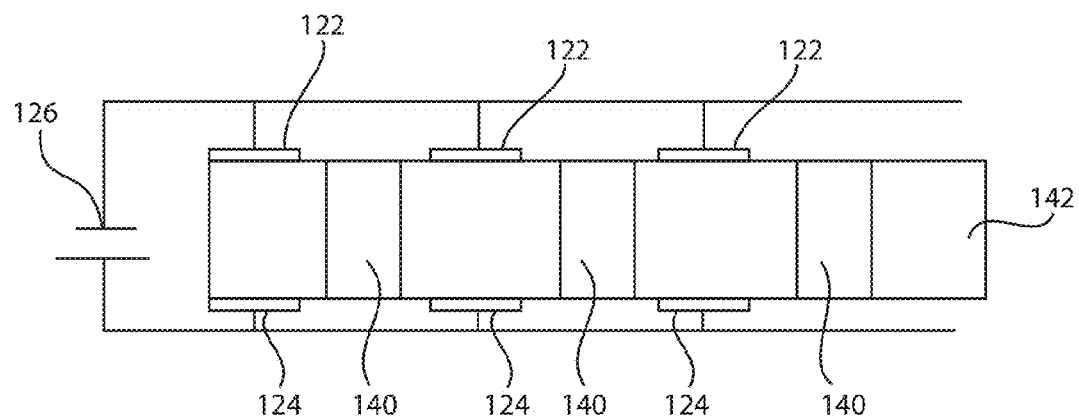
FIG. 11 is a cross-sectional view of a multiple channel toxicity sensor in accordance with another embodiment.
Figure 12:
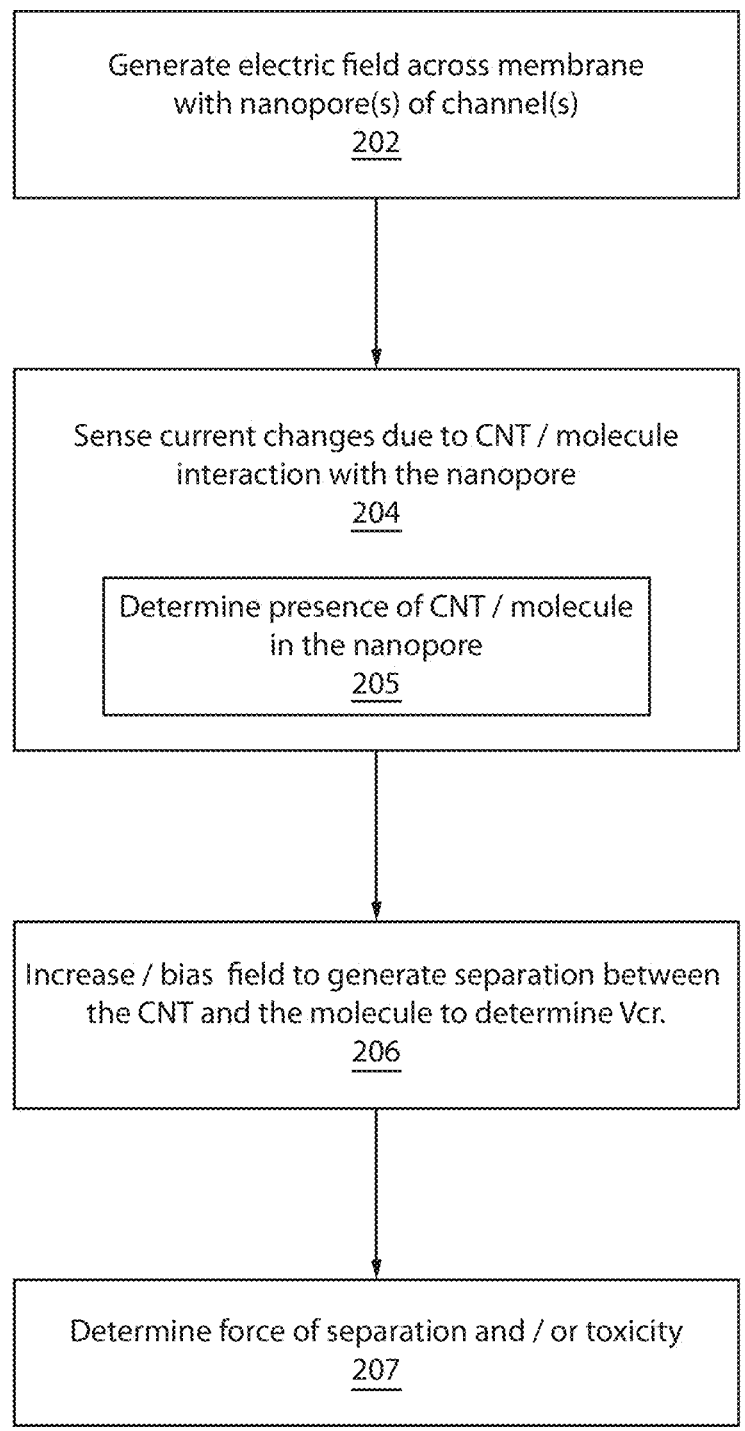
FIG. 12 is a block/flow diagram showing a method for nanosensing in accordance with illustrative embodiments.

Referring to FIG. 10, in another embodiment, multiple nanopores 114 may be employed through a same membrane 142. The nanopores 114 function as parallel paths to process CNT-protein complexes more rapidly. A battery 126 and electrodes 122, 124 are dispersed or distributed to create the electric field.

Referring to FIG. 8, in another embodiment, instead of multiple nanopores 114, multiple channels 140 may be employed.

Referring to FIG. 9, a method for detecting molecule characteristics using nanopores or channels is illustratively shown. It should be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems (e.g., circuitry, memory) that perform the specified functions or acts, or combinations of special purpose hardware and computer instructions.

In block 202, an electric field is generated across a membrane having an opening to drive charged carbon nanotubes through the opening. The opening is configured to permit the charged carbon nanotube to pass but to block a molecule attached to the carbon nanotube in the presence of the electric field. The opening is filled with an electrolytic solution. In one embodiment, the opening may include one or more nanopores and/or one or more channels.

In block 204, current changes are sensed due to charged carbon nanotubes passing through the opening. The current changes are proportional to a force of separation between the carbon nanotube and the molecule. The molecule may include a protein. In block 205, sensing includes measuring current drops and durations to determine the presence of the CNT/molecule complex in the nanopore.

In block 206, the electric field is increased/biased to reach and determine $V_{cr}$. In block 207, the force of separation is determined by comparing $V_{cr}$ to a chart or table or computing the force from an equation. The force of separation (or binding affinity) is proportional to toxicity, which is one of the molecule characteristics to be determined. The charged carbon nanotube may include a closed functionalized end having charged chemical groups.

Increasing the biasing value based on sensed current changes may include: determining a critical voltage value at which separation occurs between the carbon nanotube and the molecule. This $V_{cr}$ value can be compared to a graph or other index system to determine a characteristic based on the interaction strength. The characteristic may include binding affinity, toxicity, etc. The toxicity measured may include the toxicity of a CNT to a protein.

Having described preferred embodiments for a nanopore sensor for detecting interactions between molecules (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for detecting molecule characteristics, comprising:

generating an electric field across a membrane having an opening to drive charged carbon nanotubes through the opening, the opening being configured to permit the charged carbon nanotube to pass but to block a molecule attached to the carbon nanotube, the opening being filled with an electrolytic solution;

sensing current changes due to charged carbon nanotubes passing into or through the opening;

biasing the electric field to measure a voltage at a point of separation at an interface between the carbon nanotube and the molecule, wherein the point of separation is located at the carbon nanotube; and correlating the voltage to measure a characteristic of the molecule.

2. The method as recited in claim 1, wherein the opening includes one of a nanopore and a channel.

3. The method as recited in claim 1, wherein sensing includes measuring current drops and durations to determine when to bias the electric field.

4. The method as recited in claim 1, wherein the molecule includes a protein and the molecule characteristics include a toxicity.

5. The method as recited in claim 1, wherein the charged carbon nanotube includes a closed functionalized end having charged chemical groups.

6. The method as recited in claim 1, wherein biasing the electric field includes increasing a biasing value to determine a critical voltage value at which separation occurs between the carbon nanotube and the molecule to infer interaction strength.

* * * * *